US006373053B1

(12) United States Patent
Choo et al.

(10) Patent No.: US 6,373,053 B1
(45) Date of Patent: Apr. 16, 2002

(54) ANALYSIS OF CD-SEM SIGNAL TO DETECT SCUMMED/CLOSED CONTACT HOLES AND LINES

(75) Inventors: Bryan K. Choo, Mountain View; Bhanwar Singh, Morgan Hill; Sanjay K. Yedur, Santa Clara; Khoi A. Phan, San Jose, all of CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 09/495,281

(22) Filed: Jan. 31, 2000

(51) Int. Cl.[7] .................... G01N 23/00; G21K 7/00
(52) U.S. Cl. .................................................. 250/310
(58) Field of Search ..................... 250/304, 492.21, 250/310; 438/17; 355/67, 53; 382/149

(56) References Cited

U.S. PATENT DOCUMENTS

| | | | |
|---|---|---|---|
| 5,097,430 A | | 3/1992 | Birang |
| 5,331,370 A | * | 7/1994 | Rosner et al. ............... 355/53 |
| 5,801,821 A | | 9/1998 | Borodovsky |
| 5,926,690 A | * | 7/1999 | Toprac et al. ............... 438/17 |
| 5,946,079 A | * | 8/1999 | Borodovsky ................. 355/67 |
| 5,952,658 A | * | 9/1999 | Shimase et al. ........... 250/309 |
| 5,964,643 A | | 10/1999 | Birang et al. |
| 6,091,846 A | * | 7/2000 | Lin et al. .................. 382/145 |
| 6,205,239 B1 | * | 3/2001 | Lin et al. .................. 382/149 |

* cited by examiner

*Primary Examiner*—Jack Berman
*Assistant Examiner*—Johnnie L Smith, II
(74) *Attorney, Agent, or Firm*—Eschweiler & Associates, LLC

(57) ABSTRACT

A system is provided for detecting scumming in a wafer. The system includes an analysis system for providing a signal corresponding to a surface portion of the wafer and a processing system operatively coupled to the analysis system. The processing system is configured to determine a shape of at least a portion of the signal and, the processing system detects scumming in the wafer based upon the shape of at least a portion of the signal.

21 Claims, 5 Drawing Sheets

| TABLE 82 | |
|---|---|
| Xi | Yi |
| 0 | 1.1 |
| 1 | 1.0 |
| 2 | .90 |
| 3 | .90 |
| 4 | 1.0 |
| 5 | 1.1 |

GRAPH 80

| TABLE 92 | |
|---|---|
| Xi | Yi |
| 0 | 3.0 |
| 1 | 1.7 |
| 2 | 1.0 |
| 3 | .90 |
| 4 | 1.4 |
| 5 | 3.0 |

GRAPH 90

ANALYSIS OF CD-SEM SIGNAL TO DETECT SCUMMED/CLOSED CONTACT HOLES AND LINES

FIELD OF THE INVENTION

The present invention generally relates to semiconductor processing, and in particular to a system and method for detecting wafer lines and contacts that are scummed or partially open in conjunction with a lithography process.

BACKGROUND OF THE INVENTION

In the semiconductor industry, there is a continuing trend toward higher device densities. To achieve these high densities there has been and continues to be efforts toward scaling down the device dimensions (e.g., at submicron levels) on semiconductor wafers. In order to accomplish such high device packing density, smaller and smaller features sizes are required. This may include the width and spacing of interconnecting lines, spacing and diameter of contact holes, and the surface geometry such as comers and edges of various features.

The requirement of small features with close spacing between adjacent features requires high resolution photolithographic processes. In general, lithography refers to processes for pattern transfer between various media. It is a technique used for integrated circuit fabrication in which a silicon slice, the wafer, is coated uniformly with a radiation-sensitive film, the resist, and an exposing source (such as optical light, x-rays, etc.) illuminates selected areas of the surface through an intervening master template, the mask, for a particular pattern. The lithographic coating is generally a radiation-sensitive coating suitable for receiving a projected image of the subject pattern. Once the image is projected, it is indelibly formed in the coating. The projected image may be either a negative or a positive image of the subject pattern. Exposure of the coating through a photomask causes the image area to become either more or less soluble (depending on the coating) in a particular solvent developer. The more soluble areas are removed in the developing process to leave the pattern image in the coating as less soluble polymer.

Due to the extremely fine patterns which are exposed on the photoresist, Scanning Electron Microscopes (SEMs) are often employed to analyze and measure critical dimensions resulting from the lithographic process. Critical dimensions include the size of minimum features across the wafer such as linewidth, spacing, and contact dimensions. Although SEMs have been effective in providing quantitative measurement information related to critical dimensions of a wafer, they have not been as effective in providing qualitative analytical information regarding process related issues.

A particular process related issue is known as scumming and is generally related to the resolution of the image pattern, and may occur with either negative or positive resists. Scumming may result when a feature is underexposed, has poor focus, or is simply too small to print (e.g., mask defect or a subnominal test structure). As a result of the aforementioned resolution problems, line edges may not be well defined and scumming may occur between the lines or within a contact hole. This results in the areas between the lines and within the contact openings to only be partially open.

Conventional analytical CD-SEM systems for measuring critical dimensions of wafers often fail to detect lines and contact openings that may be scummed or only partially open. Thus, poorly processed wafers may provide adequate critical dimension measurements yet evade detection of scummed lines and contacts. For example, a scummed contact opening may be measured for the width of the contact opening. Even though the contact opening may only be partially open, conventional CD-SEM systems often indicate adequate width dimensions despite the fact that the contact opening may be defective.

It would therefore be desirable to have a system and/or method which substantially increases the probability that scummed lines and contacts will be detected during the measurement of critical dimensions.

SUMMARY OF THE INVENTION

The present invention is directed toward a system and method for detecting scummed lines and contacts in a film resulting from a lithographic process. A signal is provided by an SEM system during critical dimension measurements. By applying analytical signal processing techniques to the signal, a determination is made as to the quality of the underlying film undergoing the critical dimension measurement. By employing such techniques, various lithographic processes may be characterized effectively. This results in identifying a lithographic process which provides increased manufacturing yields and increased integrated circuit performance.

More particularly, the present invention performs a curve fitting analysis to the signal received from the SEM system during critical dimension measurements. It has been found that scummed lines and contacts produce a curved or generally nonlinear signal response over a portion of the received signal. In contrast, a generally flat signal response is provided by a properly manufactured wafer. Mathematical regression analysis provides a methodology for determining the amount of curvature or flatness in the measured signal whereby scummed lines and contacts may be detected by determining if a portion of the signal is above a predetermined threshold of curvature during the critical dimension measurement. It is noted that the invention disclosed herein may be applied to substantially any system that provides a shaped signal based on the scanning or measurement of a wafer surface.

To the accomplishment of the foregoing and related ends, the invention, then, comprises the features hereinafter fully described. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

DETAILED DESCRIPTION OF THE INVENTION

Figure 1:
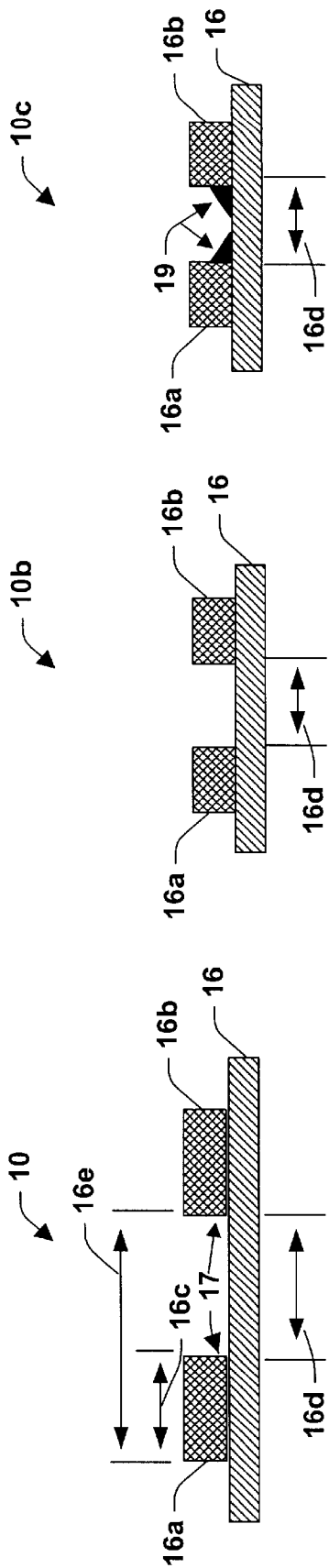
FIG. 1a is a cross section diagram of a wafer illustrating critical dimension measurements in accordance with the present invention.
FIG. 1b is a diagram of a non-scummed wafer and corresponding signal in accordance with the present invention.
FIG. 1c is a diagram of a scummed wafer and corresponding signal in accordance with the present invention.

The present invention will now be described with reference to the drawings, wherein like reference numerals are used to refer to like elements throughout.

The present invention provides a system and methodology to detect poorly processed and/or scummed lines and contacts in a processed film. The system is preferably implemented in a software system as part of a critical dimension scanning electron microscope (CD-SEM). The software system analyzes the SEM signal concurrently with a critical dimension (CD) algorithm, thus resulting in substantially no loss in system throughput. Although the present invention is described in reference to a CD-SEM system, it is to be appreciated that the system and methodology described below may be applied to substantially any analytical system providing a shaped signal based on the geometry and/or topology of the surface being measured.

Referring initially to FIG. 1a, a cross section of a printed wafer 10 is shown. Subsequent to the printing process, two lines 16a and 16b of a thin film layer remain in contact with a substrate layer 16. Various critical dimensions of the wafer 10, typically measured by an SEM or like system, are shown in order to characterize the efficacy of the lithographic process employed to form the various features. Dimension 16c, for example, depicts a linewidth measurement of the line 16a. Dimension 16d depicts an open contact region or space between lines 16a and 16b, and a pitch dimension 16e generally refers to a line density on the substrate 16. The wafer 10 illustrates a portion of a properly resolved integrated circuit having no scum between or near lines 16a and 16b. As a result, edges 17 near lines 16a and 16b are clearly defined and the space between the lines is substantially open.

Turning now to FIG. 1b, an SEM signal 18 represents a surface measurement of the space 16d of a properly resolved portion of a wafer 10b. A conventional SEM system may provide a critical dimension measurement of the space 16d as 1.8 microns, for example. During critical dimension measurements of the space 16d, a substantially flat portion 18a of the SEM signal 18 is received when the space or region 16d between lines 16a and 16b is substantially open. Referring now to FIG. 1c, a wafer 10c is shown with a scum 19 between lines 16a and 16b. An SEM signal 18b is shown from the measurement of the space 16d. The signal 18b, in contrast to signal 18 in FIG. 1b, depicts a generally curved region 18c when critical dimension measurements are performed and the scum 19 is present. Even though the region 16d is only partially open, a conventional SEM system when measuring scummed lines and spaces may determine an acceptable critical dimension, however. For example, a detected signal width 18d from signal 18 depicted in FIG. 1b substantially compares to a signal width 18f from signal 18b depicted in FIG. 1c. Thus, conventional SEM systems may detect the presence of a contact hole yet fail to provide information regarding contact hole quality. Consequently, conventional SEM systems frequently fail to detect that poorly resolved contacts are present. If scum is left undetected, performance and possibly failure of the integrated circuit may likely occur. Thus, the present invention, performs a signal based analysis during the critical dimension measurement to determine potential defects in the underlying wafer caused by the lithographic process.

Figure 2:
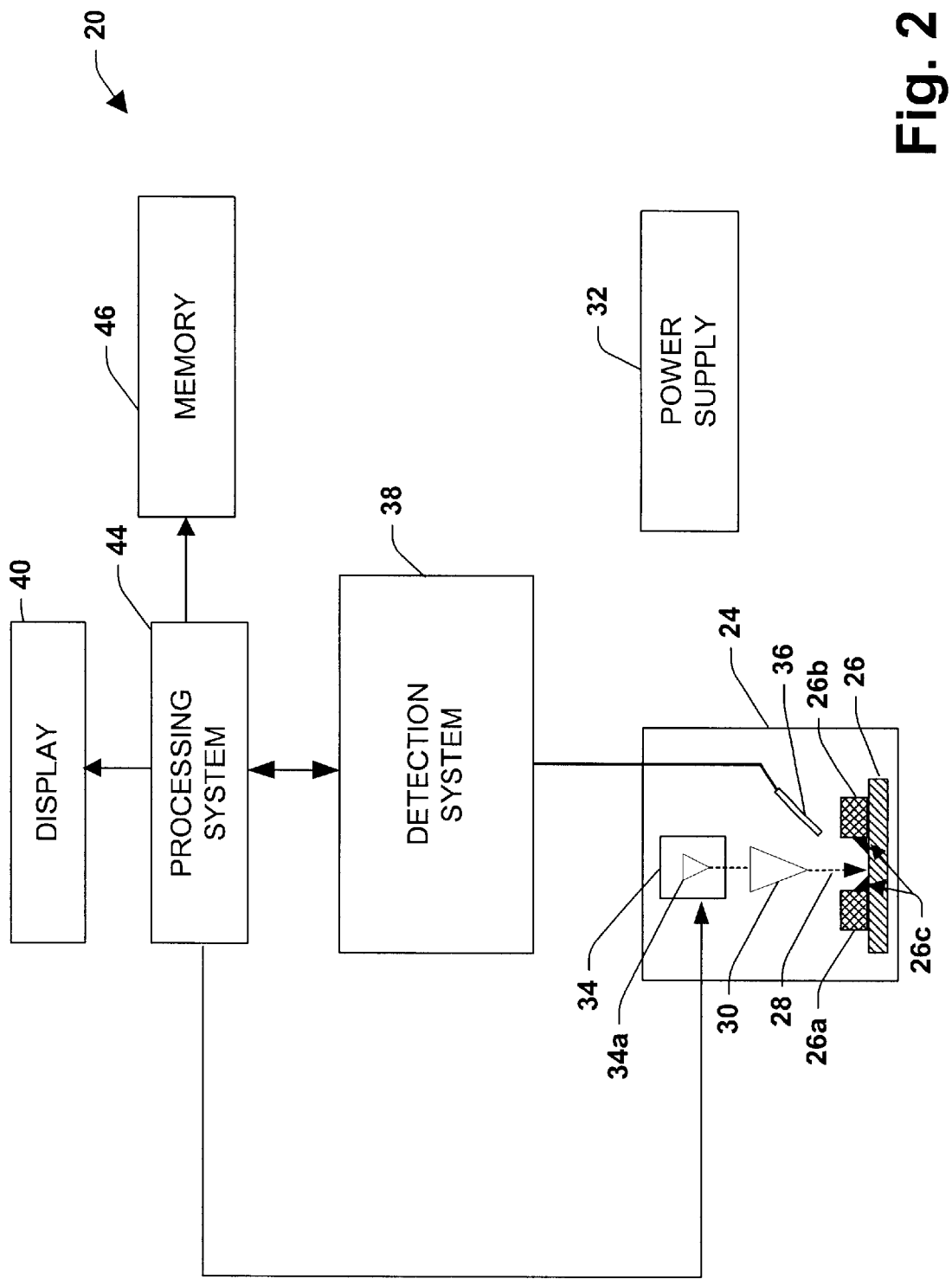
FIG. 2 is a schematic block diagram of an exemplary CD-SEM system for determining scumming in accordance with the present invention.

Now referring to FIG. 2, a CD-SEM system 20 is shown for detecting scummed lines and contacts in accordance with the present invention. The system includes a chamber 24 for housing a wafer 26. An electron beam 28 is directed from an electromagnetic lens 30 toward the wafer 26. The electron beam 28 is created from high voltage supplied by a power supply 32 associated with a beam generating system 34 which includes an emission element 34a. Various directing, focusing, and scanning elements (not shown) in the beam generating system 34 guide the electron beam 28 from the emission element 34a to the electromagnetic lens 30. The electron beam particles may be accelerated to energies from about 500 eV to 40 Kev. When the electron beam 28 strikes the surface of the wafer 26, electrons and x-rays are emitted which are detected by a detector 36 and are provided to a detection system 38. The detection system 38 provides digitized detector signals to a processing system 44 for performing conventional critical dimension measurements and signal analysis in accordance with the present invention.

Electrons which are emitted from the surface of the wafer 26 which are most useful for critical dimension imaging are known as secondary electrons and provide a substantial amount of the signal current received by the detector 36. A critical dimension image may also be directed to a display 40 by the processing system 44. The processing system 44, in addition to analyzing data received by the detection system 38, synchronizes the scanning of the display 40 with electron beam scanning of the wafer 26 to provide the image. Contrast of the displayed image is related to variations in the flux of electrons arriving at the detector 36 and is related to the yield of emitted electrons from the surface of the wafer 26 to the incident electrons from the electron beam 28.

The wafer 26 depicted in FIG. 2 shows a cross section of an etched portion of the wafer including two lines 26a and 26b. In a properly resolved wafer, the region between lines 26a and 26b would be substantially free from scum. As shown in FIG. 2, however, scum residuals 26c remain between lines 26a and 26b. As will be described in more detail below, when scum exists in regions on the wafer, a substantially curved electronic signal is provided to the detection system 38 from the detector 36. Conversely, a substantially flat or square signal is received by the detection and measuring system 38 when the regions near the lines 26a and 26b are substantially open.

The detection system 38 receives the electron emissions from the wafer surface via the detector 36 and preferably digitizes the information for the processing system 44. In addition, the detection system 38 may also provide filtering or other signal processing of the received signal, as described in more detail below. The processing system 44 provides critical dimension information to the display 40 and/or stores information in a memory 46. In accordance with the present invention, the processing system 44 includes a curve fitting software system for determining if contaminants such as scum residuals 26c are present between or near the lines 26a and 26b. A processor (not shown) is included in the processing system 44 for controlling the beam generating system 34, providing critical dimension measurements, and for performing signal analysis in accordance with the present invention. It is to be appreciated that a plurality of processors and/or processing systems may be included as part of and/or external to the CD-SEM system 20 for performing signal analysis in accordance with the present invention. As will be described in more detail below, signals received from wafer surface measurements are digitized and analyzed as a data set. By analyzing the data, for example, by employing regression mathematics to the data set, a shape for the data set may be determined and scummed regions of the wafer may be rejected based on a predetermined criteria for the shape of the data set.

The processor in the processing system 44 is programmed to control and operate the various components within the CD-SEM system 20 in order to carry out the various functions described herein. The processor may be any of a plurality of processors, such as the AMD Athlon, K6 or other type architecture processors. The manner in which the processor may be programmed to carry out the functions relating to the present invention will be readily apparent to those having ordinary skill in the art based on the description provided herein and are omitted herein for the sake of brevity.

A memory 46 is also included in the system 20. The memory 46 is operatively coupled to the processing system 44 and serves to store program code executed by the processor for carrying out operating functions of the system 20 as described herein. The memory 46 also serves as a storage medium for temporarily storing information such as curve fitting data, critical dimension data, statistical data, and other data which may be employed in carrying out the present invention.

The power supply 32 also provides operating power to the CD-SEM system 20 along with providing a high voltage to the beam generating system 34. Any suitable power supply (e.g., linear, switching) may be employed to carry out the present invention.

Figure 3:
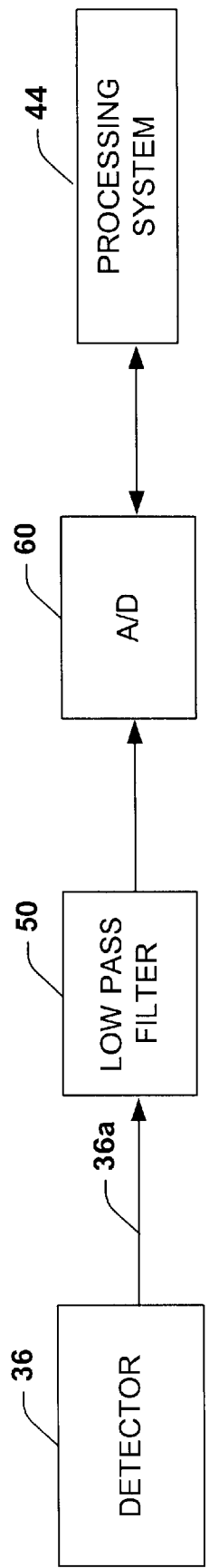
FIG. 3 is more detailed schematic block diagram of a detection system in accordance with the present invention.

Now referring to FIG. 3, a more detailed drawing of an exemplary detection system 38 of FIG. 2 is shown. A potentially noisy electrical output signal 36a from the detector is coupled to the input of a low pass filter 50. The low pass filter 50 is shown for illustrative purposes and may be implemented in hardware or as part of a digital low pass filter algorithm in the processing system 44. The signal 36a may need to be smoothed by a low pass filter before subsequent shape analysis occurs by the present invention. An analog to digital (A/D) converter 60, receives the analog signal provided by the detector 36 and/or low pass filter 50 and converts the signal to digital form. The A/D 60 provides binary data to the processing system 44 which performs critical dimension measurements and performs signal analysis in accordance with the present invention. The binary data may be stored in memory for subsequent signal analysis or may be analyzed concurrently with the critical dimension measurement.

Now referring to FIGS. 4a through 4d, an exemplary signal analysis in accordance with a preferred embodiment of the present invention is illustrated. As described above, the present invention is preferably implemented as a software system operating in conjunction with the CD algorithm of the SEM system. It is to be appreciated however, that the present invention may be implemented as part of a separate processing system. For example, the critical dimension signal data may be passed to a post or concurrent processing system to determine the quality of the particular region measured. It is further to be appreciated that the present invention may be directed to other systems which provide signals based on surface geometry and/or topological measurements.

Figure 4A:
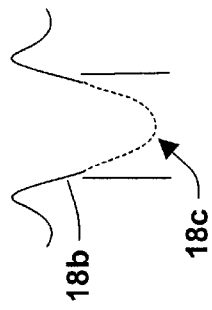
FIGS. 4a–4b depict generally flat and curved signals in accordance with the present invention.
Figure 4B:
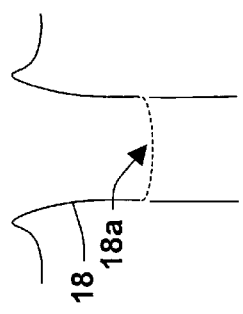

FIGS. 4a and 4b depict a received signal from a properly resolved and poorly resolved region respectively. A portion of signal 18 is shown as a relatively flat portion 18a. In FIG. 4b, a relatively curved portion 18c is shown as part of signal 18b. The size and amount of the received signal portions to be analyzed may be predetermined, as may be desired. For example, the entire signal width of signal 18 and 18b may consist of 100 samples. It may be predetermined that the middle 50 samples, for example, are provided to the signal analysis system for a determination of the quality of the measured region. As will be described in more detail below, by analyzing the shape of at least a portion of the received sample, the present invention is able to determine if the measured region has been properly resolved.

Figure 4C:
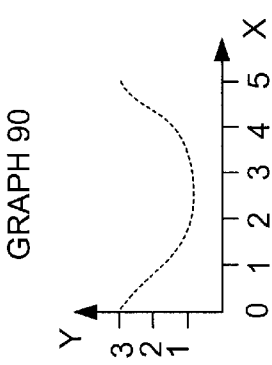
FIGS. 4c–4d illustrate generally flat and curved signal data in accordance with the present invention.

Referring now to FIG. 4c, an exemplary set of data points of the flat region 18a are shown in graphical and tabular formats to illustrate the analytical aspects of the present invention. For the sake of brevity, six data points $X_0$ through $X_5$, each having a value of Y, will be described in accordance with the present invention. Graph 80 depicts the generally flat portion 18a of the received signal. Arbitrary graduations are shown along the Y axis with values ranging from 0 to 3. It is noted that the Y axis dimensions may be scaled to accommodate substantially any system. In the present invention, the Y axis represents the magnitude of the received signal voltage, and along the X axis, sampled points are recorded at particular points in time. The values of X may be discrete integers representing time points for sampled voltages having particular values of Y. The sampling points may be increased to substantially any number for the desired accuracy of the signal quality determination.

In accordance with the present invention, a curve fitting analysis is applied to the received data to determine the signal shape (e.g., flat shape, parabolic shape) in the measured region. Many techniques are available for fitting particular data to a linear region or to a curve. The present invention applies a linear and/or polynomial regression to determine the amount of flatness or curvature in the desired region. It is to be appreciated, however, that many other well known methods for curve fitting and/or regression may be applied to determine the shape of the received data and each such method is contemplated as falling within the scope of the present invention.

Data depicted by the Graph 80 in FIG. 4c is illustrated in Table 82. The values of Y at given points of X can be seen to be at or near a value of 1.0 indicating a general propensity of flatness in the received data. It is noted that the data is preferably to be analyzed with respect to the entire data set. For example, if the data were merely analyzed at the endpoints $X_0$ or $X_5$ as being below a certain value (e.g., 1.2), curvature of the data would be undetected if values $X_3$ and $X_4$ were much less than one. This would potentially allow scummed regions to escape detection.

According to one particular embodiment of the present invention, a "best fit" criteria is employed for determining whether a given data set is more closely modeled by a linear or polynomial equation. The best fit may be determined by performing a statistical analysis on the actual data in conjunction with predicted data values of the linear or polynomial equations. Based upon the outcome of the statistical analysis, a determination is made as to whether the data is more closely related to the linear model and/or to the higher order polynomial model. For example, if the data is relatively linear (e.g., flat signal response), the statistical analysis will show a substantially higher correlation (e.g., better fit, best fit criteria closer to 1 as described in more detail below) for the linear model than the polynomial model. By selecting a threshold of correlation for the best fit criteria, scumming may be detected when the correlation is above/ below a predetermined threshold for the linear model or above/below a predetermined threshold for the polynomial model.

A set of equations will now be described in more detail to further illustrate the workings of the present invention. A linear equation for fitting a set of data is shown in Equation 1.

$y = a_0 + a_1 X + e$ (wherein e represents the residual or error between the mathematical model and the actual data). Equation 1:

This equation may be extended for equations of a higher order as shown in Equation 2.

$y = a_0 + a_1 X + a_2 X^2 + \ldots + a_m X^m + e$  Equation 2:

An approach to fitting the actual data (determining the coefficients to the above equations) to Equations 1 and 2, is to minimize the sum of the squares of the residuals as shown in Equations 3 and 4.

Equation 3:
$$Sr = \sum_{i=1}^{n} e_i^2 = \sum_{i=1}^{n} (y_i - a_0 - a_1 X)^2$$

wherein Sr represents the sum of the squares of the residuals.

Equation 4:
$$Sr = \sum_{i=1}^{n} (y_i - a_0 - a_1 X - a_2 X^2 - \ldots - a_m X^m)^2$$

From these equations, a coefficient of determination may be determined. The coefficient of determination is then employed to determine whether the data is best fit to a linear equation and/or polynomial equation. The coefficient of determination or $r^2$ maybe determined as follows:

$r^2 = (S_t - S_r)/S_t$.  Equation 5:

wherein St is the total sum of the squares around the mean of the dependent variable y and represents the uncertainty associated with the dependent variable prior to regression. If $r^2$ is close to the value of 1 after applying Equation 5, then the actual data is closely or best fit to the linear or polynomial equations described above. The following discussion is related to a numerical example to illustrate the workings of the present invention.

Curvature of the received data may be obtained, for example, by fitting an $m^{th}$ order polynomial to the received data as shown in Equation 2. Alternatively, Equation 1 may applied to determine if the data points are best fit to a linear equation. For example, a $2^{nd}$ order polynomial (generally having a parabolic or curved shape) may be fit to the received data samples at $X_0$ through $X_5$. Equation 2 and Equation 4 may be manipulated to form a set of equations for determining the coefficients of an $m^{th}$ order polynomial to fit the given data as shown in Equations 6 through 8.

$a_0 n + a_1 \Sigma Xi + a_2 \Sigma Xi^2 + \ldots + a_m \Sigma Xi^m = \Sigma Yi$  Equation 6:

$a_0 \Sigma Xi + a_1 \Sigma Xi^2 + a_2 \Sigma Xi^3 + \ldots + a_m \Sigma Xi^{m-1} = \Sigma XiYi$  Equation 7:

$a_0 \Sigma Xi^2 a_1 \Sigma Xi^3 + a_2 \Sigma Xi^4 + \ldots a_m \Sigma Xi^{m+2} = \Sigma Xi^2 Yi$  Equation 8:

whereby n is the number of points to be fit, and m is the degree to which the data points are to be fit.

From the given data in Table 82, and a $2^{nd}$ degree equation illustrated for example, the following determinations for the above equations may be obtained:

m=2, n=6, $\Sigma Xi = 15$, $\Sigma Xi^2 = 55$, $\Sigma Xi^3 = 225$, $\Sigma Xi^4 = 979$, $\Sigma Yi = 6$, $\Sigma XiYi = 15$, $\Sigma Xi^2 Yi = 56.2$, $\Sigma(Yi - Y^2)^2 = 0.04$, $\Sigma(Y_i - a_0 - a_1 Xi - a_2 Xi^2)^2 = 0.01272$. (Note: Determined after coefficients)

From which the following linear equations may be written as shown in equations 6 through 8 above:

$6a_0 + 15a_1 + 55a_2 = 6$  Equation 9:

$15a_0 + 55a_1 + 225a_2 = 15$  Equation 10:

$55a_0 + 225a_1 + 979a_2 = 56.2$  Equation 11:

Equations 9 through 11 may be solved employing conventional Gaussian elimination techniques. The solution to the second order equation is shown in equation 12 below.

$y = 0.032X^2 - 0.161X + 1.11$  Equation 11:

$r^2 = 0.964$.  Equation 13:

From equation 12, it can be observed that the data from Table 82 can be fit to a second order equation having a slight parabolic curve. By selecting a threshold for $r^2$ or $a^2$, a determination may be made as to the quality of the wafer sample. Alternatively, the $X^2$ coefficient of 0.032 is so slight that one may deduce a high degree of flatness from the fitted equation indicating that the given data as a group approximates a straight line. The above data points are given as an illustrative example to demonstrate the workings of the current invention. The given data points from a properly processed wafer may very well follow a straight line (e.g., all points have the same value) and thus, the $X^2$ term in Equation 12 would be 0. It is also to be appreciated, as shown from the generalized equations above, that higher order equations may be fit to given data points if so desired.

Figure 4D:
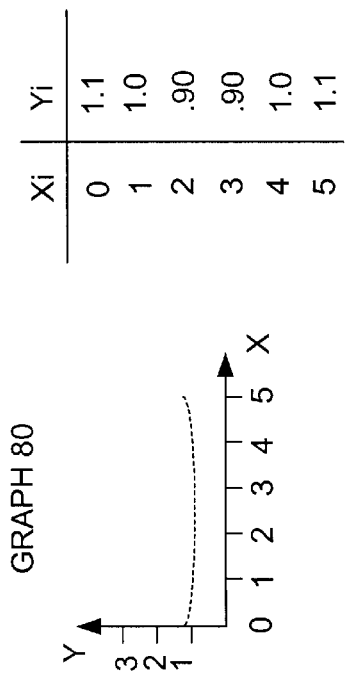

Now turning to FIG. 4d, a Graph 90 of data points from a scummed or poorly resolved wafer is shown. The data points (shown in Table 92) may represent the curved signal as depicted in FIG. 4b. As described above, the received set of data may be fit to a curve to determine the degree of curvature and ultimately, whether the measured wafer surface has been compromised by scumming. A similar curvature analysis for the data in Table 92 is shown below.

From the given data in Table 92, the following determinations for the above equations may be obtained:

m=2, n=6, $\Sigma Xi = 15$, $\Sigma Xi^2 = 225$, $\Sigma Xi^4 = 979$, $\Sigma Yi = 11$, $\Sigma XiYi = 27$, $\Sigma Xi^2 Yi = 111,2$, $\Sigma(Yi - Y)^2 = 72.45$, $\Sigma(Y_i - a_0 - a_1 \ Xi - a_2 \ Xi^2)^2 = 0.04513$. (Note: Determined after coefficients)

The following linear equations may be written as shown in Equations 14 through 16:

$6a_0 + 15a_1 + 55a_2 = 11$  Equation 14:

$15a_0 + 55a_1 + 225a_2 = 27$  Equation 15:

$55a_0 + 225a_1 + 979a_2 = 111.2$  Equation 16:

Equations 14 through 16 may be solved employing conventional Gaussian elimination techniques. The solution to the second order equation is shown in equation 17 below.

$$y = 0.344X^2 - 1.75X + 3.05 \quad \text{Equation 17:}$$

$$r^2 = 0.990. \quad \text{Equation 18:}$$

From equation 16, it can be observed that the data from Table 92 may be fit to a second order equation having a much greater parabolic curve than the data from Table 82 above. As shown in Equation 17, $r^2$ is very close to 1 indicating that the data is very closely fit to the curved equation. The $X^2$ coefficient of 0.344 in Equation 16 is about 10 times higher than demonstrated in Equation 11 above. Thus, one may deduce a high degree of curvature from the fitted equation indicating that the given data as a group approximates a curve.

By predetermining the amount of curvature allowable in any given data set, a user may set a desired threshold whereby wafer regions producing signals below a predetermined curvature threshold are accepted and signals above a predetermined curvature threshold are rejected. As mentioned above, threshold determinations are preferably made concurrently with the critical dimension measurement.

As an alternative to the above described embodiments, both a linear and polynomial regression may be performed on a given data set. An $r^2$ correlation is then determined for each regression. Scumming is then determined based on whether the correlation coefficients from the linear and polynomial equations are closely matched. For example, if after performing the correlation function $r^2$ for both the linear and polynomial regressions, and if the $r^2$ results were both within a predetermined amount of equivalence, a determination could be made that scumming was substantially not present. Likewise, if the $r^2$ results were substantially dissimilar, then a determination could be made that scumming was substantially present.

Figure 5:
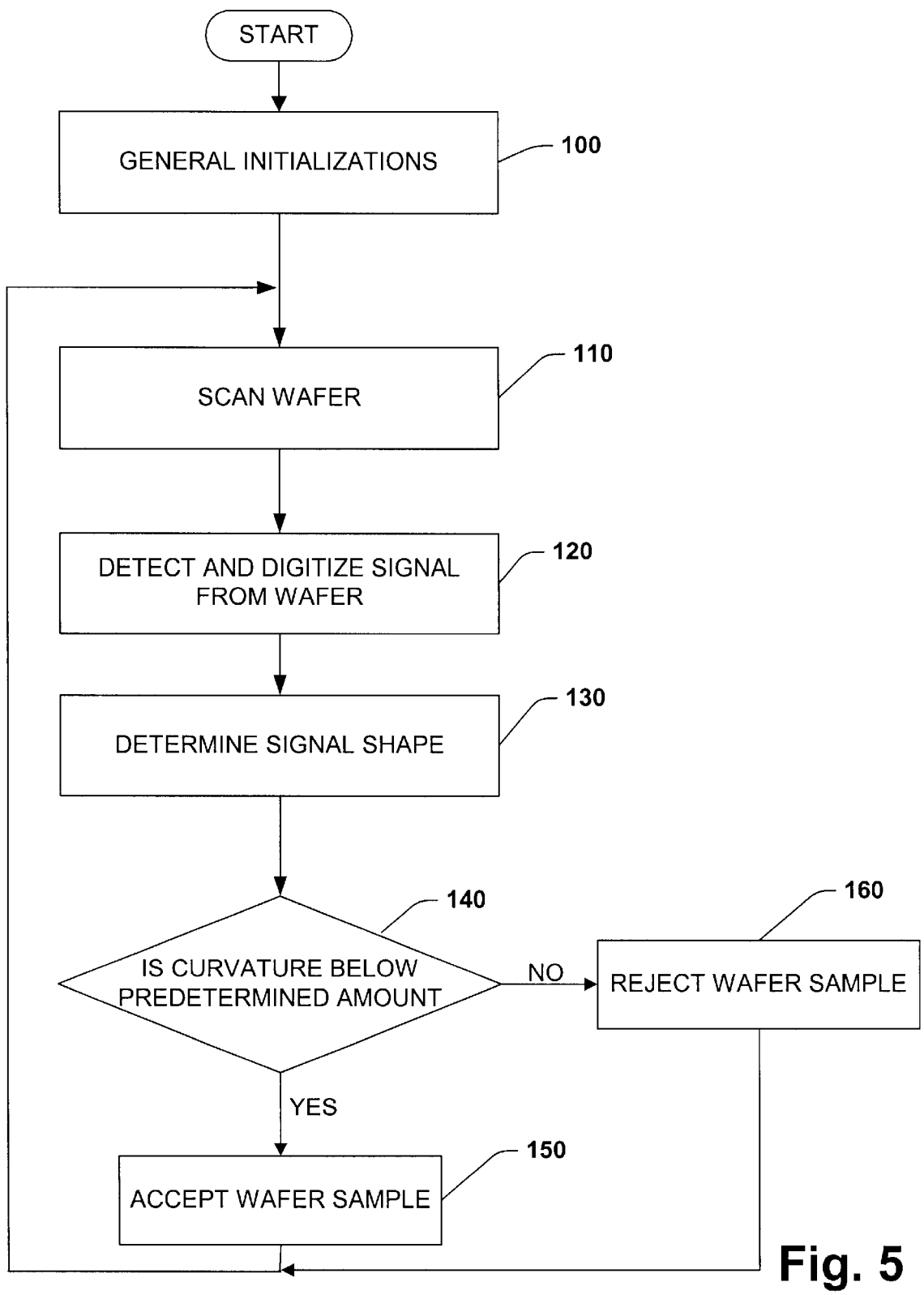
FIG. 5 is a flow chart diagram illustrating a methodology for carrying out the present invention.

FIG. 5 is a flow chart diagram illustrating a methodology for carrying out the present invention. In step 100, the processing system 44 performs general initializations to the CD-SEM system 20 in preparation of measuring a portion of a wafer sample. In step 110, the processing system initiates scanning of the wafer by directing a beam generating system 34 to scan the wafer sample. In step 120, a signal is received by the detector 36 and passed to the detection system 38. The signal preferably is then digitized before being directed to the processing system 44. In step 130, the processing system 44 analyzes the received signal shape by fitting a curve to the set of data received from the detection and measuring system 38. In step 140, a determination is made based on whether curvature of the data is below a predetermined threshold. If so, the processing system 44 accepts the currently measured wafer sample in step 150 and then proceeds back to step 110 to perform another measurement. If the curvature is above the predetermined threshold, the wafer sample is rejected in step 160 and the processing system 44 proceeds back to step 110 to perform another measurement.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described components (assemblies, devices, circuits, etc.), the terms (including a reference to a "means") used to describe such components are intended to correspond, unless otherwise indicated, to any component which performs the specified function of the described component (i.e., that is functionally equivalent), even though not structurally equivalent to the disclosed structure which performs the function in the herein illustrated exemplary embodiments of the invention. In addition, while a particular feature of the invention may have been disclosed with respect to only one of several embodiments, such feature may be combined with one or more other features of the other embodiments as may be desired and advantageous for any given or particular application.

What is claimed is:

1. A system for detecting scumming in a wafer, comprising:
   an analysis system operable to analyze a surface portion of a wafer and provide a signal corresponding to a surface portion of the wafer; and
   a processing system operatively coupled to the analysis system;
   wherein the processing system is configured to determine a shape of at least a portion of the signal provided by the analysis system;
   wherein the processing system is further configured to perform curve fitting on a set of data corresponding to the signal; and
   wherein the processing system is further configured to detect scumming in the wafer based upon the shape of the at least a portion of the signal.

2. The system of claim 1, wherein the analysis system comprises a CD-SEM.

3. The system of claim 1, wherein the curve fitting comprises mathematical regression.

4. A system for detecting scumming in a wafer, comprising:
   an analysis system operable to analyze a surface portion of a wafer and provide a signal corresponding to a surface portion of the wafer; and
   a processing system operatively coupled to the analysis system;
   wherein the processing system is configured to determine a shape of at least a portion of the signal provided by the analysis system; and
   wherein the processing system is further configured to detect scumming in the wafer based upon predetermined criteria corresponding to the shape of the at least a portion of the signal.

5. The system of claim 4, wherein the predetermined criteria is based upon curvature of a set of data.

6. The system of claim 4, wherein the predetermined criteria is based upon equivalence of correlation criteria from a polynomial and linear regression.

7. A system for detecting scumming in a wafer, comprising:
   an analysis system operable to analyze a surface portion of a wafer and provide a signal corresponding to a surface portion of the wafer; and
   a processing system operatively coupled to the analysis system;
   wherein the processing system is configured to determine a shape of at least a portion of the signal provided by the analysis system; and
   wherein the processing system is further configured to detect scumming in the wafer based upon the shape of the at least a portion of the signal, wherein the shape of the signal from a scummed wafer is curved.

8. A system for detecting scumming in a wafer, comprising:
   an analysis system operable to analyze a surface portion of a wafer and provide a signal corresponding to a surface portion of the wafer; and a processing system operatively coupled to the analysis system;

wherein the processing system is configured to determine a shape of at least a portion of the signal provided by the analysis system; and wherein the processing system is further configured to detect scumming in the wafer based upon the shape of the at least a portion of the signal, wherein the shape of the signal from a non-scummed wafer is flat.

9. A system for detecting scumming in a wafer, comprising:

an analysis system operable to analyze a surface portion of a wafer and provide a signal corresponding to a surface portion of the wafer; and a processing system operatively coupled to the analysis system;

wherein the processing system is configured to determine a shape of at least a portion of the signal provided by the analysis system;

wherein the processing system is further configured to detect scumming in the wafer based upon the shape of the at least a portion of the signal, and wherein the processing system is configured to determine scumming by quantitatively measuring a curvature of the at least a portion of the signal, and wherein the processing system is further configured to compare the curvature to a predetermined threshold, and wherein the processing system is still further configured to decide whether to accept or reject a sample based on whether the curvature is less than or greater than the predetermined threshold.

10. The system of claim 9, wherein the system for providing a signal is a CD-SEM.

11. A system for detecting scumming in a wafer, comprising:

a system for analyzing a wafer and providing a signal corresponding to a surface of the wafer;

a system operatively coupled to the analysis system for determining a shape of at least a portion of the signal provided by the analysis system; and a system operably coupled to the signal determination system for detecting scumming in the wafer based upon the shape of the at least a portion of the signal; and wherein the shape is determined by curve fitting a set of data corresponding to the signal.

12. The system of claim 11, wherein the curve fitting comprises a mathematical regression.

13. The system of claim 11, wherein the signal is provided during critical dimension measurements.

14. A system for detecting scumming in a wafer, comprising:

a system for analyzing a wafer and providing a signal corresponding to a surface of the wafer;

a system operatively coupled to the analysis system for determining a shape of at least a portion of the signal provided by the analysis system; and a system operably coupled to the signal determination system for detecting scumming in the wafer based upon the shape of the at least a portion of the signal;

wherein the shape of the signal from a scummed wafer is curved.

15. A system for detecting scumming in a wafer, comprising:

a system for analyzing a wafer and providing a signal corresponding to a surface of the wafer;

a system operatively coupled to the analysis system for determining a shape of at least a portion of the signal provided by the analysis system; and a system operably coupled to the signal determination system for detecting scumming in the wafer based upon the shape of the at least a portion of the signal; and wherein the shape of the signal from a non-scummed wafer is flat.

16. A CD-SEM system for detecting scumming in a wafer, comprising:

a lens for directing electrons toward a surface of the wafer;

a detector for providing a signal based upon electrons detected and received from the surface of the wafer in response to the electrons directed to the wafer surface by the lens; and a processing system operably coupled to the detector and configured to determine a shape of at least a portion of the signal;

wherein the processing system is further configured to detect scumming in the wafer based upon the determined shape of the at least a portion of the signal; and wherein the shape is determined by curve fitting a set of data corresponding to the signal.

17. The CD-SEM system of claim 16, wherein the curve fitting comprises a mathematical regression.

18. The CD-SEM system of claim 16, wherein the signal is provided during critical dimension measurements.

19. The CD-SEM system of claim 16, wherein the processing system is configured to detect scumming based upon a predetermined criteria of curvature of a set of data from the at least a portion of the signal.

20. The CD-SEM system of claim 16, wherein the shape of the signal from a scummed wafer is curved.

21. The CD-SEM system of claim 16, wherein the shape of the signal from a non-scummed wafer is flat.

* * * * *

UNITED STATES PATENT AND TRADEMARK OFFICE
CERTIFICATE OF CORRECTION

PATENT NO.   : 6,373,053 B1
DATED        : April 16, 2002
INVENTOR(S)  : Bryan K. Choo, Bhanwar Singh, Sanjay K. Yedur and Khoi A. Phan It is certified that error appears in the above-identified patent and that said Letters Patent is hereby corrected as shown below:

Column 1,
Line 20, please replace the word "comers" with the word -- corners --.

Column 8,
Line 50, please replace the line "m=2, n=6, $\Sigma Xi=15$, $\Sigma Xi^2=225$, $\Sigma Xi^4=979$, $\Sigma Yi=11$," with the line: -- m=2, n=6, $\Sigma Xi=15$, $\Sigma Xi^2=55$, $\Sigma Xi^3=225$, $\Sigma Xi^4=979$, $\Sigma Yi=11$, --

Signed and Sealed this

Tenth Day of December, 2002

JAMES E. ROGAN
*Director of the United States Patent and Trademark Office*